United States Patent
Kim et al.

(10) Patent No.: US 11,786,298 B2
(45) Date of Patent: Oct. 17, 2023

(54) EPIDURAL CATHETER WITH RF GENERATION FUNCTION

(71) Applicant: JUVENUI Co., LTD, Seongnam-si (KR)

(72) Inventors: Hyun Hong Kim, Seoul (KR); Jae Suk Sung, Suwon-si (KR)

(73) Assignee: JUVENUI Co., LTD, Seongnam-si (KR)

( * ) Notice: Subject to any disclaimer, the term of this patent is extended or adjusted under 35 U.S.C. 154(b) by 2 days.

(21) Appl. No.: 16/921,947

(22) Filed: Jul. 7, 2020

(65) Prior Publication Data

US 2021/0030466 A1    Feb. 4, 2021

(30) Foreign Application Priority Data

Aug. 2, 2019   (KR) .......................... 10-2019-0094563

(51) Int. Cl.
*A61B 18/14* (2006.01)
*A61B 18/12* (2006.01)
(Continued)

(52) U.S. Cl.
CPC ...... *A61B 18/1492* (2013.01); *A61B 18/1206* (2013.01); *A61B 2018/0044* (2013.01);
(Continued)

(58) Field of Classification Search
CPC ............ A61B 18/1492; A61B 18/1206; A61B 2018/0044; A61B 2018/00708; A61B 2018/0091; A61B 2018/1405; A61B 2018/1497; A61B 2018/1467; A61B 2018/1417; A61B 2018/126; A61M 25/0136; A61M 25/0147; A61M 2025/0007

See application file for complete search history.

(56) References Cited

U.S. PATENT DOCUMENTS

2005/0090816 A1 *  4/2005  McClurken ............ A61B 17/32
                                                      606/49
2009/0163915 A1 *  6/2009  Potter ................ A61B 18/1492
                                                      606/41
(Continued)

FOREIGN PATENT DOCUMENTS

JP   2005-508658 A    4/2005
KR   10-2012-0038174 A  4/2012

*Primary Examiner* — Michael F Peffley
*Assistant Examiner* — Samantha M Good
(74) *Attorney, Agent, or Firm* — PARK, KM & SUH, LLC

(57) ABSTRACT

Disclosed herein is an epidural catheter with an RF generation function. More specifically, the epidural catheter with an RF generation function may include a main body, an inserting part being connected to the main body and being inserted inside a physical body, and a manipulating part being provided in the main body and being connected to the inserting part or an internal assembly part of the inserting part, so as to manipulate the inserting part or to perform a function of the inserting part, wherein two steering wires may be interpolated in the inserting part, the two steering wires being manipulated by the manipulating part so as to allow flexion of the inserting part to be controlled, and wherein, by allowing power status to be turned on/off using the main body as medium, the steering wires may act as electrodes.

7 Claims, 9 Drawing Sheets

(51) Int. Cl.
*A61B 18/00* (2006.01)
*A61M 25/01* (2006.01)

(52) U.S. Cl.
CPC ........... *A61B 2018/0091* (2013.01); *A61B 2018/00708* (2013.01); *A61B 2018/1405* (2013.01); *A61B 2018/1497* (2013.01); *A61M 25/0147* (2013.01)

(56) References Cited

U.S. PATENT DOCUMENTS

| | | |
|---|---|---|
| 2011/0106221 A1 | 5/2011 | Neal, II et al. |
| 2015/0238248 A1* | 8/2015 | Thompson ............... H05H 1/46 606/50 |
| 2018/0014880 A1* | 1/2018 | Rioux ................ A61B 18/1492 |
| 2018/0116711 A1* | 5/2018 | Suh ................... A61B 18/1206 |
| 2019/0038349 A1* | 2/2019 | Koblish .............. A61B 5/4836 |
| 2019/0183561 A1* | 6/2019 | Hobbs ................ A61B 18/1492 |

* cited by examiner

EPIDURAL CATHETER WITH RF GENERATION FUNCTION

CROSS-REFERENCE TO RELATED APPLICATION

This application claims the benefit of the Korean Patent Application No. 10-2019-0094563, filed on Aug. 2, 2019, which is hereby incorporated by reference as if fully set forth herein.

TECHNICAL FIELD

The present invention relates to an epidural catheter with a radio frequency (RF) generation function and, most particularly, to an epidural catheter with an RF generation function integrating an RF generator with a catheter, so as to allow a treatment effect to be redoubled by supplying RF electromagnetic waves when performing an epidural medical (or surgical) treatment procedure and to allow the treatment process to be easily carried out.

BACKGROUND ART

Epidural catheter products are being broadly used for injecting medications (or drugs) for spinal pain treatment, and so on. However, since there are treatment limitations in using only the aforementioned chemical treatment method(s), recently, there has been an increase in performing RF treatments, which create an electric field by irradiating RF electromagnetic waves on nerve areas that cause pain, and which reduce pain through such electric field.

However, even though simultaneously carrying out therapeutic (or surgical) procedures using catheters and RF treatment leads to excellent results and enables simplicity in the therapeutic (or surgical) procedure to be implemented, there existed the inconvenience of having to carry out each therapeutic (or surgical) procedure separately.

Furthermore, since the direction and distribution of the radiated RF electric field cannot be adjusted, there existed a problem of being incapable of performing an accurate precision treatment according to the size or type of an affected area.

DISCLOSURE

Technical Problem

The present invention has been devised to resolve the above-described problems of the related art, and, in order to overcome treatment limitations of conventional catheter products that only inject medications (or drugs), an object of the present invention is to maximize treatment effects not only of chemical treatment methods but also in combination with electromagnetic treatment methods using radio frequency (RF), by integrating a circuit unit generating RF and RF electrodes with a medication injecting catheter product.

Additionally, another object of the present invention is to perform RF irradiation only on a wanted area so as to enhance the treatment effect, by developing a method for arbitrarily controlling the direction and distribution of an electric field being generated from RF electrodes.

Furthermore, another object of the present invention is to adjust a penetration depth of an electric field so as to enhance the treatment effect, by adopting a variable frequency circuit that changes (or varies) the generated frequency.

Technical Solution

In order to achieve the above-described technical objects of the present invention, provided herein is an epidural catheter with an RF generation function. The epidural catheter with an RF generation function may include a main body, an inserting part being connected to the main body and being inserted inside a physical body, and a manipulating part being provided in the main body and being connected to the inserting part or an internal assembly part of the inserting part, so as to manipulate the inserting part or to perform a function of the inserting part, wherein two steering wires may be interpolated in the inserting part, the two steering wires being manipulated by the manipulating part so as to allow flexion of the inserting part to be controlled, and wherein, by allowing power status to be turned on/off using the main body as medium, the steering wires may act as electrodes.

Preferably, the inserting part may be a form of a soft tube.

Preferably, the main body may be equipped with an RF generator, wherein the two steering wires may be connected to each of a cathode end and an anode end of the RF generator, and wherein the manipulating part may include a lever being connected to an opposite end of an inserting part of the steering wires, so as to pull the steering wires or release pulling of the steering wires, a switch being used to turn power on/off for the steering wires, and an RF electric current application button allowing RF electric current to be supplied to the steering wires, so as to allow the steering wires to act as RF electrodes, when the switch is an On state.

Preferably, round-type electrodes may be combined with a directional end of the inserting part of each steering wire, and the round-type electrodes may be symmetrical to one another and spaced apart from one another.

Preferably, the round-type electrodes may be deployed to be symmetrical to one another and not to contact one another, and distances between the round-type electrodes may not be the same.

Preferably, a relatively large RF magnetic field may be generated in an area where a distance between the round-type electrodes is short, and a direction and distribution of an RF electric field may be adjusted in accordance with the distance between the round-type electrodes.

Advantageous Effects

As described above, according to the present invention, in order to overcome treatment limitations of conventional catheter products that only inject medications (or drugs), the present invention is expected to maximize treatment effects not only of chemical treatment methods but also in combination with electromagnetic treatment methods using radio frequency (RF), by integrating a circuit unit generating RF and RF electrodes with a medication injecting catheter product.

Additionally, the present invention is expected to perform RF irradiation only on a wanted area so as to enhance the treatment effect, by developing a method for arbitrarily adjusting the direction and distribution of an electric field being generated from RF electrodes.

Furthermore, the present invention is expected to adjust a penetration depth of an electric field so as to enhance the treatment effect, by adopting a variable frequency circuit that changes (or varies) the generated frequency.

DETAILED DESCRIPTION OF EMBODIMENTS

Hereinafter, an exemplary embodiment of the present invention will be described in detail with reference to the accompanying drawings so that anyone skilled in the art can easily carry out the present invention. However, it shall be understood that the present invention may be embodied in different variations and that the present invention will not be limited only to the exemplary embodiment presented herein. Furthermore, it shall also be understood that parts of the invention that are irrelevant to the detailed description of the present invention have been omitted for clarity of the description of the present invention. It will be apparent that throughout this specification similar numeral references have been given to similar parts of the invention.

Throughout the entire specification of the present invention, when a particular part is said to "include" a particular element, this indicates that, unless specified otherwise, the corresponding part may further include another element (or other elements), and, therefore, this does not indicate that the corresponding part excludes the other element(s).

Additionally, terms indicated as " . . . unit", " . . . part", " . . . device", " . . . module", and so on, indicates a unit executing or processing at least one function or operation.

In the present invention, since the catheter is a disclosed art, and, accordingly, since the inserting part of the catheter, steering wires being interpolated in the inserting part, and so on, are also a disclosed art, detailed description of the configuration, operating method(s), connection structure(s) of this art will be omitted. Additionally, since the essential configuration elements, which are needed for carrying out the process of generating RF electromagnetic waves from an RF generator and performing treatment by using the resulting RF electric current, are also a disclosed art, detailed description of the same will be omitted.

More specifically, the present invention will be described while focusing on characteristic elements that are needed to combine the catheter and the RF generator to a single body.

Figure 1:
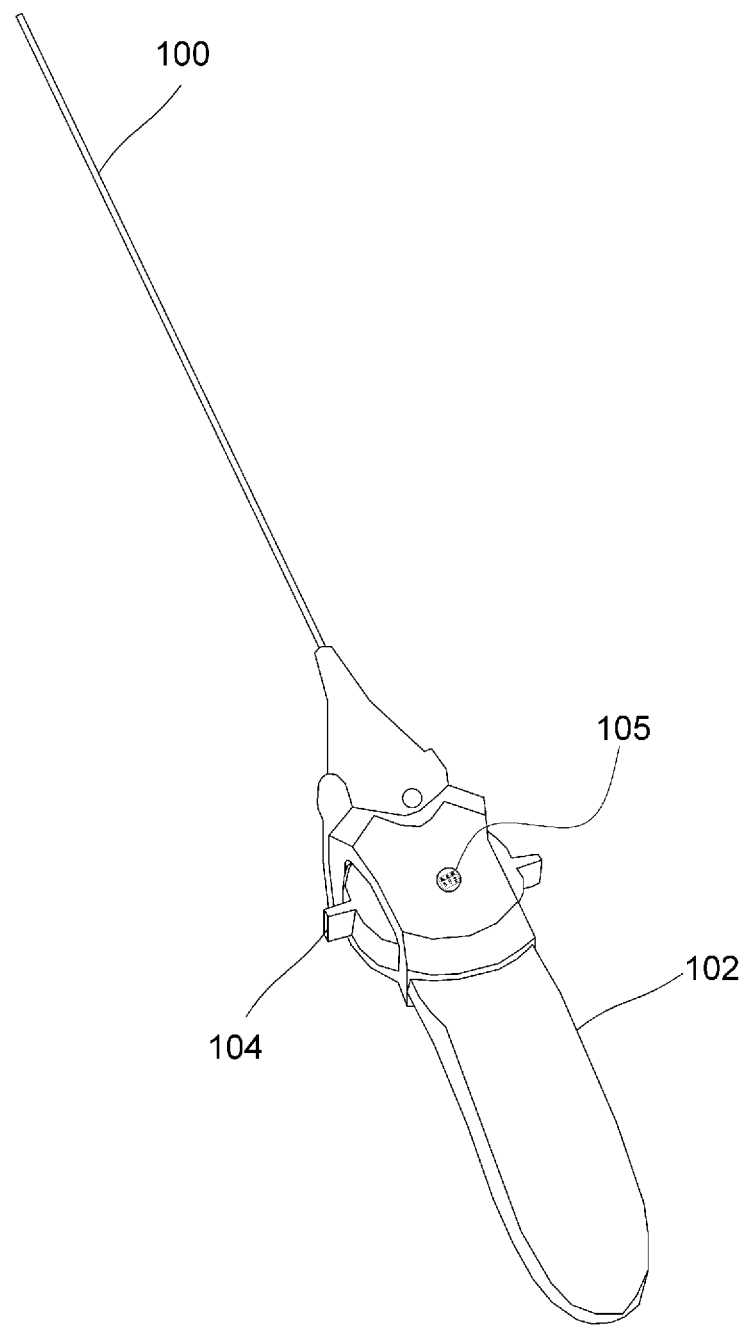
FIG. 1 is a diagram showing a conventional epidural catheter and an RF generator.
Figure 2:
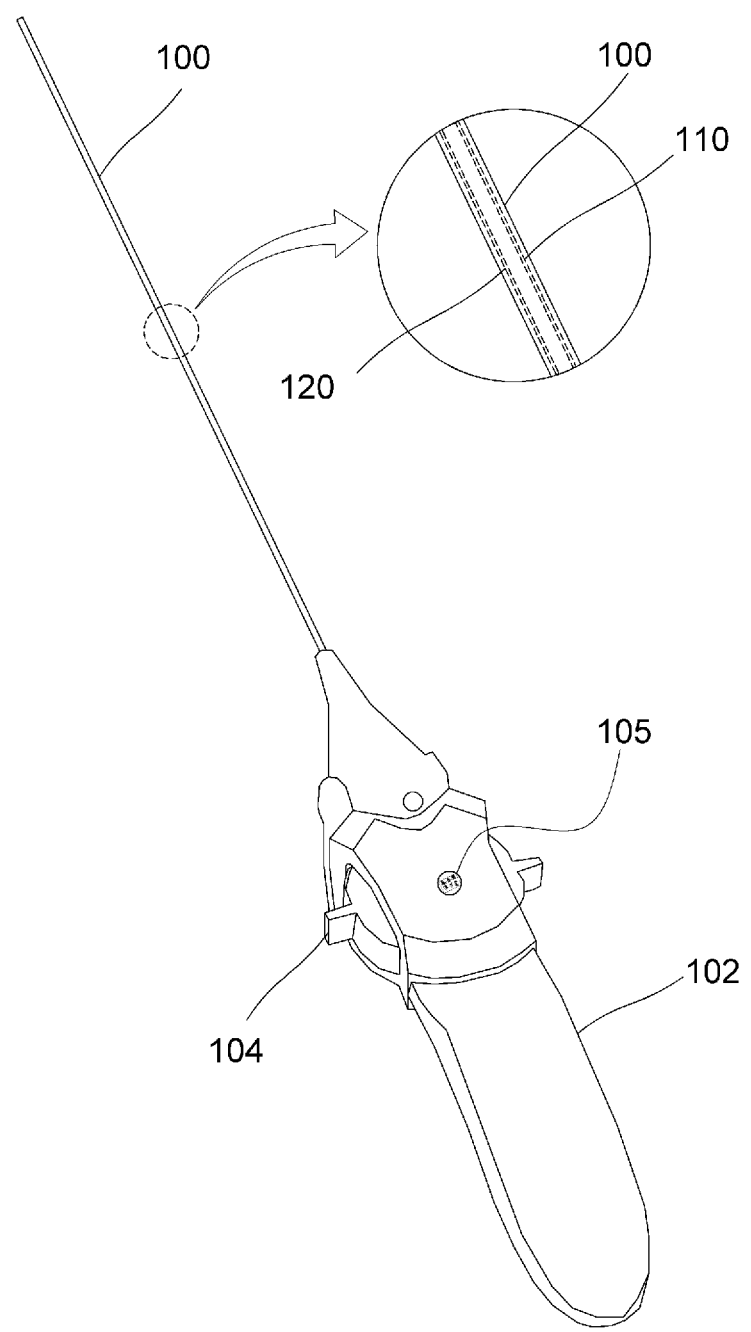
FIG. 2 is a mimetic diagram showing a form of an epidural catheter having an RF generator function according to an exemplary embodiment of the present invention.
Figure 3:
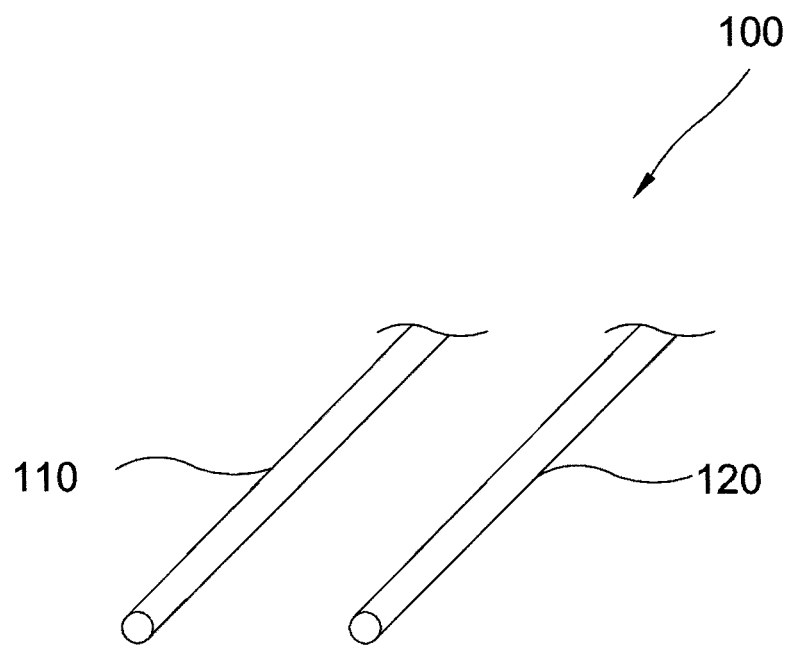
FIG. 3 is a mimetic diagram showing a form of simultaneously using steering wires of the epidural catheter as RF electrodes according to an exemplary embodiment of the present invention.
Figure 4:
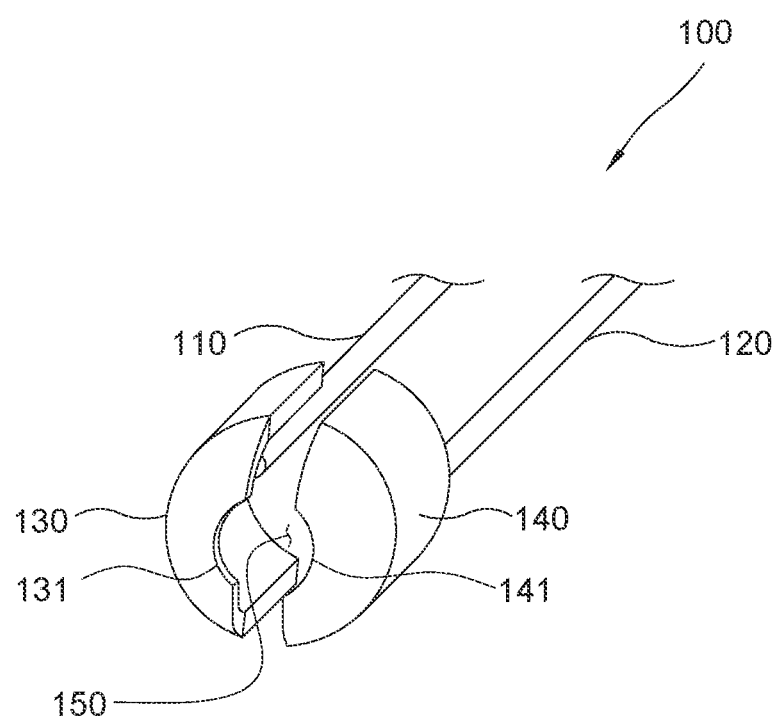
FIG. 4 is a mimetic diagram showing an example of additionally adding round-type electrodes to the steering wires of the epidural catheter according to an exemplary embodiment of the present invention.
Figure 5A:
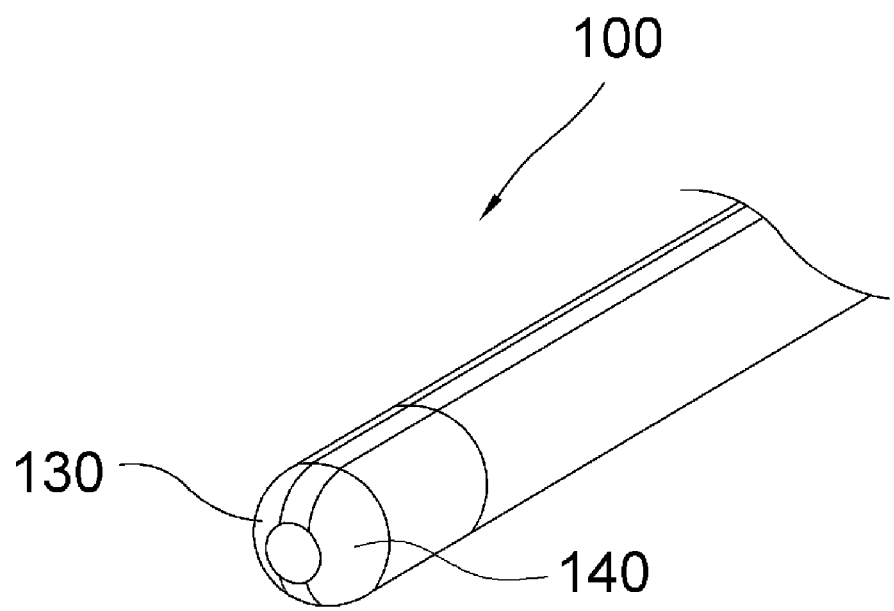
FIGS. 5A to 5C are mimetic diagrams showing an example of controlling an RF electric field by forming an anisotropic gap between two round-type electrodes formed at the electrode ends of the epidural catheter according to an exemplary embodiment of the present invention.
Figure 5B:
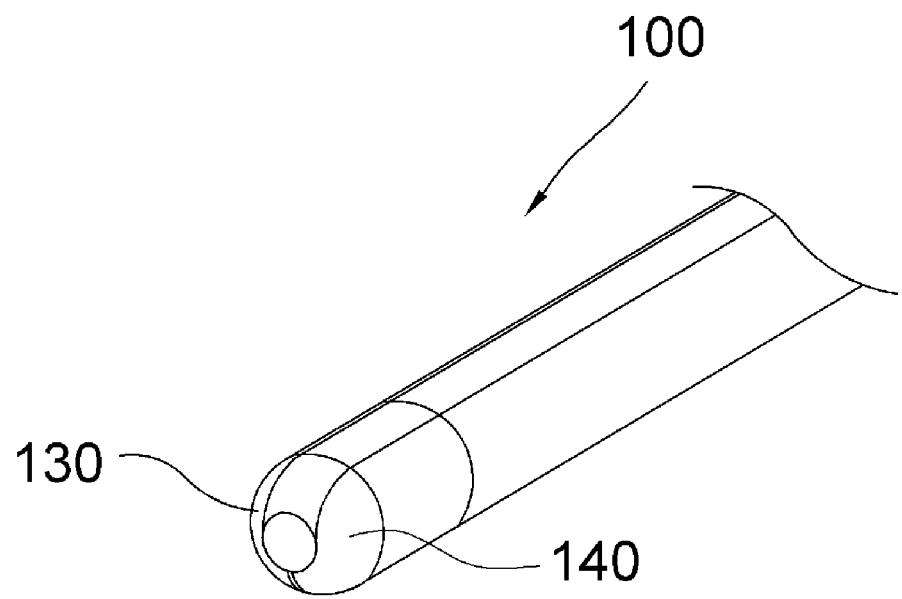
Figure 5C:
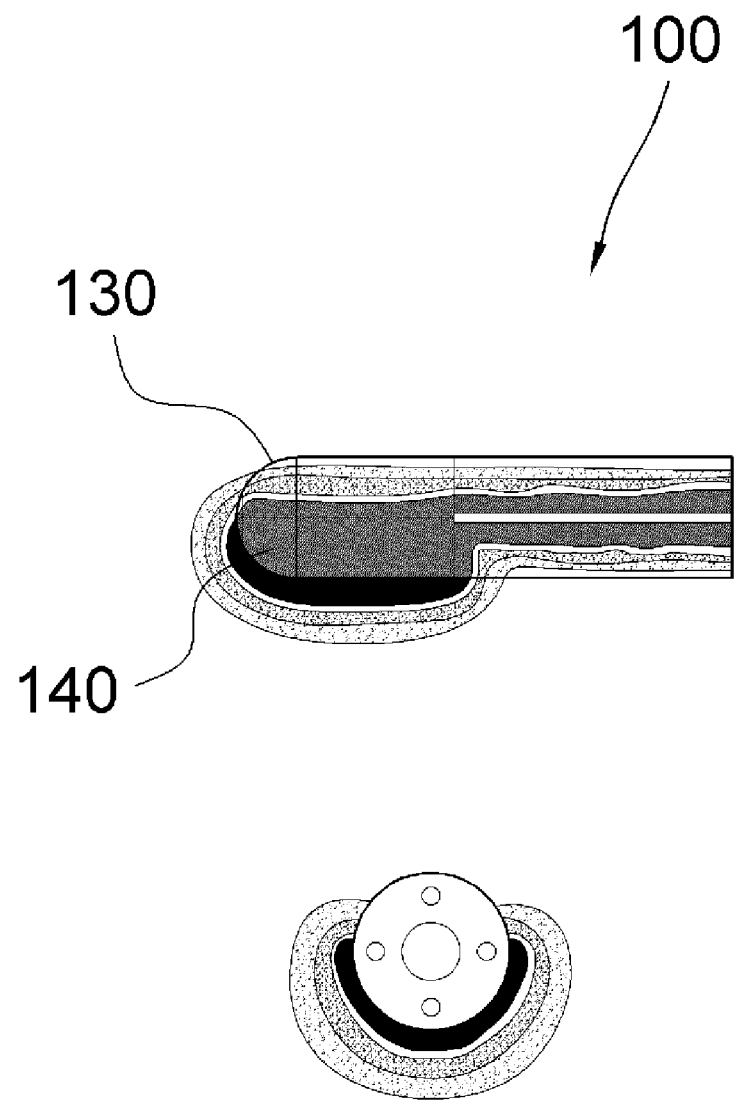
Figure 6:
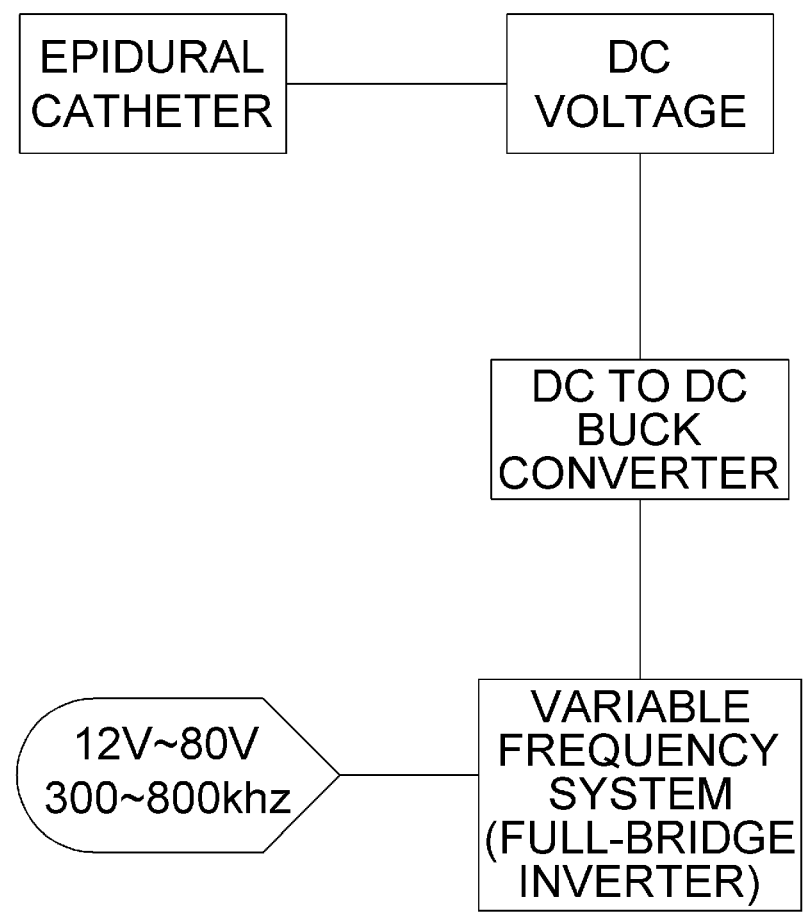
FIG. 6 is a block diagram enabling an RF frequency to be varied and supplied to the epidural catheter according to an exemplary embodiment of the present invention.
Figure 7:
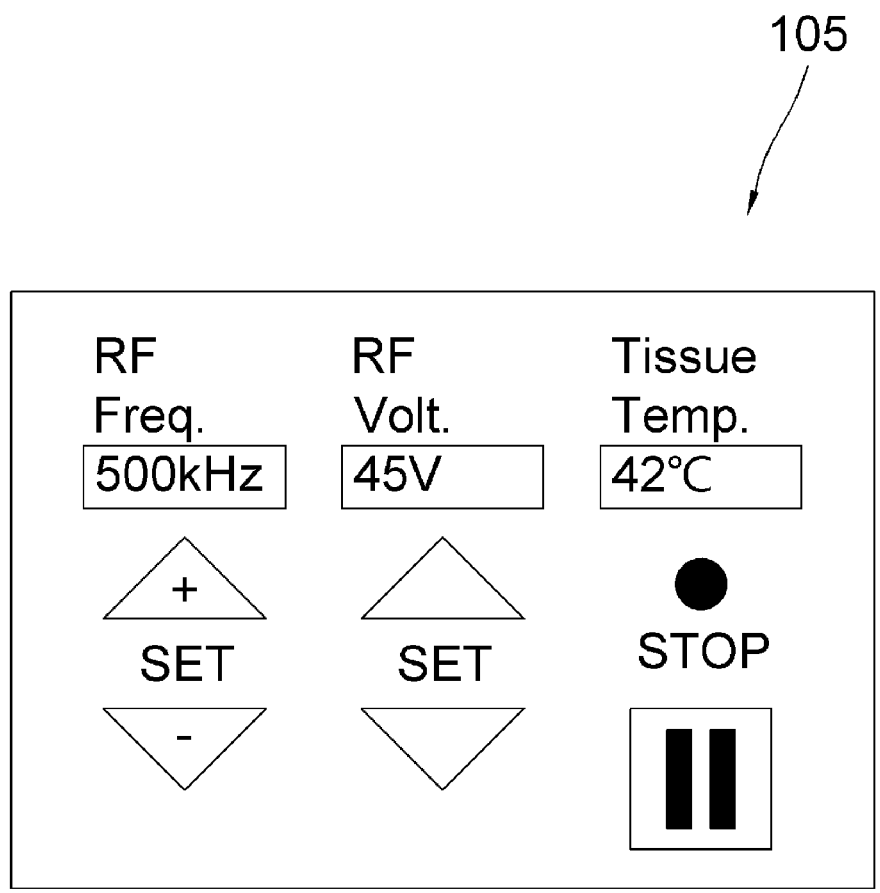
FIG. 7 is a mimetic diagram showing an example of equipping the epidural catheter with a touch panel and using a user interface (UI) to manipulate, through the touch panel, the catheter according to the exemplary embodiment of the present invention.

FIG. 1 is a diagram showing a conventional epidural catheter and an RF generator. FIG. 2 is a mimetic diagram showing a form of an epidural catheter having an RF generator function according to an exemplary embodiment of the present invention. FIG. 3 is a mimetic diagram showing a form of simultaneously using steering wires of the epidural catheter as RF electrodes according to an exemplary embodiment of the present invention. FIG. 4 is a mimetic diagram showing an example of additionally adding round-type electrodes to the steering wires of the epidural catheter according to an exemplary embodiment of the present invention. FIGS. 5A to 5C are mimetic diagrams showing an example of controlling an RF electric field by forming an anisotropic gap between two round-type electrodes formed at the electrode ends of the epidural catheter according to an exemplary embodiment of the present invention. FIG. 6 is a block diagram enabling an RF frequency to be varied and supplied to the epidural catheter according to an exemplary embodiment of the present invention. And, FIG. 7 is a mimetic diagram showing an example of equipping the epidural catheter with a touch panel and using a user interface (UI) to manipulate, through the touch panel, the catheter according to the exemplary embodiment of the present invention.

The epidural catheter with an RF generation function according to the present invention may include a main body, an inserting part being connected to the main body and being inserted inside a physical body, and a manipulating part being provided in the main body and being connected to the inserting part or an internal assembly part of the inserting part, so as to manipulate the inserting part or to perform a function of the inserting part, wherein two steering wires may be interpolated in the inserting part, the two steering wires being manipulated by the manipulating part so as to allow flexion of the inserting part to be controlled, and wherein, by allowing power status to be turned on/off using the main body as medium, the steering wires may act as electrodes.

Generally, the inserting part (100) is a form of a soft tube. Generally, the soft tube has a round cross-section, and this is to facilitate the inserting part (100) to be inserted into a patient's body. In case the inserting part (100) is formed of a soft material, this allows the inserting part (100) to easily change directions inside the patient's body.

Herein, the main body (102), the inserting part (100), the manipulating part (104), and so on, are also equipped in the related art catheter. However, as a catheter, the concept of using the steering wires (110, 120) within the inserting part (100) as electrodes has not existed in the prior art methods. And, therefore, this is one of the characteristics of the present invention.

The present invention has various characteristics. A first characteristic is that RF treatment may be integrated and performed by the catheter. A second characteristic is that, for such RF treatment, RF electrodes (130, 140) are separately provided at an end of the catheter inserting part (100). A third characteristic is that the RF electrodes (130, 140) are equipped while maintaining a diameter of the conventional inserting part (100) without any modification. And, a fourth characteristic is that, by devising a unique method for manipulating the RF electrodes (130, 140), the direction and distribution of an magnetic field may be adjusted.

Meanwhile, the main body (102) is connected to an external power source, or equipped with an RF generator having it own internal power source, such as a battery, and so on, and the two steering wires (110, 120) are connected to each of a cathode end and an anode end of the RF generator. The manipulating part (104) may include a lever being connected to an opposite end of an inserting part (100) of the steering wires (110, 120), so as to pull the steering wires (110, 120) or release pulling of the steering wires (110, 120), a switch being used to turn power on/off for the steering wires (110, 120), and an RF electric current application button allowing RF electric current to be supplied to the steering wires (110, 120), so as to allow the steering wires (110, 120) to act as RF electrodes (130, 140), when the switch is an On state.

More specifically, the present invention is basically equipped with steering wires (110, 120), a lever, and so on, which are also the configuration parts of the related art catheter. Herein, the present invention is configured to additionally include a switch being used to turn power on/off for the steering wires (110, 120), and an RF electric current application button allowing RF electric current to be supplied to the steering wires (110, 120), so as to allow the steering wires (110, 120) to act as RF electrodes (130, 140), when the switch is an On state.

FIG. 1 illustrates a diagram showing a conventional epidural catheter and an RF generator. The epidural catheter reduces pain by inserting an inserting part (100) of the catheter inside a human body, and by injecting medication being supplied from an external source and withdrawn from the inserting part (100).

And, the RF generator is a device that is used separately from the catheter. The RF generator generates an RF electric field near nerve parts that cause pain inside the human body and applies RF electromagnetic waves. Thus, the RF generator reduces pain by disrupting the nervous system.

As described above, the conventional technologies belong to different technical fields, and such technologies are used on patients via separate devices (or apparatuses). Therefore, if the two technologies are integrated, the therapeutic (or surgical) procedure may be expected to be performed more conveniently.

FIG. 2 illustrates a mimetic diagram showing a form of an epidural catheter having an RF generator function according to an exemplary embodiment of the present invention.

This is an integration of an RF generator circuit and electrodes to the epidural catheter described in FIG. 1, which not only performs chemical pain treatment using medication (or drugs) but also electromagnetic treatment using an RF electric field.

For this, two problems shall be technically resolved. One is to minimize the size of configuration elements, such as circuit, electrodes, and so on, in order to equip the RF generator inside the epidural catheter. And, the other is to implement an ultra-low-cost disposable catheter by extracting only the minimum essential functions of a high-priced RF generator, which costs approximately 10 million Korean won. In other words, the catheter according to the present invention aims to be disposable after a single usage while being equipped with an RF generator.

FIG. 3 illustrates a mimetic diagram showing a form of simultaneously using steering wires (110, 120) of the epidural catheter as RF electrodes according to an exemplary embodiment of the present invention.

In order to configure an RF generator, not only a frequency generating circuit but also RF electrodes (130, 140) for irradiating an electric field shall be configured. Herein, however, it is very difficult to provide space for equipping the conventional epidural catheter with RF electrodes (130, 140). This is because, in order to perform treatment by using RF electric current, an electrode configuration needs to be provided to the inserting part (100), which is inserted into a physical body. However, if electrodes generating RF electromagnetic waves are configured separately and installed inside the inserting part (100), so as to be parallel to the conventional inserting part (100) configuration, a problem of having the diameter of the inserting part (100) become larger may occur. The inserting part (100) is a configuration element that is inserted inside the physical body of a patient, and, according to the developmental trend of this technology, the diameter of the inserting part (100) needs to be implemented to a smaller size. And, therefore, an extension of the diameter of the inserting part (100) means reversing (or going against) such developmental trend. If the diameter of the inserting part (100) is extended (or increased), most particularly, when using an epidural catheter, this may lead to critical side effects during or after the therapeutic (or surgical) procedure. And, such danger (or risk) increases in accordance with the extension (or increase) in the diameter of the conventional inserting part (100). Therefore, it will be preferable to maintain the diameter of the conventional inserting part (100) as much as possible, while interpolating the electrodes (130, 140) for supplying the RF electromagnetic waves.

In the present invention, in order to resolve this problem, the steering wires (130, 140) for moving the inserting part (100) of the epidural catheter from left-to-right (or right-to-left) inside the physical body have been mutually used for forming RF electrodes (130, 140). Herein, by using the steering wires (110, 120) as RF electrodes (130, 140) at the same time, the spatial problem may be resolved. More specifically, by connecting the steering wires (110, 120) to an external power source, electric current (or power) may flow into the steering wires (110, 120), and by additionally adding small-sized electrodes on the steering wires (110, 120) within a range of not further increasing the diameter of the inserting part (100), when performing therapeutic (or surgical) procedures by using a catheter, treatment using RF electric currents may be performed simultaneously.

FIG. 4 illustrates a mimetic diagram showing an example of additionally adding round-type electrodes (130, 140), each having a cylindrical shape, to the ends of the steering wires (110, 120), which are being used as electrodes (130, 140), in the epidural catheter according to an exemplary embodiment of the present invention.

The round-type electrodes (130, 140) are deployed to be symmetrical to one another, and the two electrodes (130, 140) do not contact one another.

By providing the epidural catheter with the above-described round-type electrodes (130, 140), and by equipping the round-type electrodes (130, 140) inside the inserting part (100), while maintaining the initial diameter of the conventional catheter inserting part (100) without any modification, RF electric currents generated from the catheter may be used more easily.

As described above, by adding additional round-type electrodes (130, 140) to an end of each steering wire (110, 120), the space within the catheter main body (102) may maintain its initial size. In the conventional epidural catheter product, round-type electrodes (130, 140) do not exist, and the electrodes (130, 140) are formed to be the same as the steering wires (110, 120), without any modification. In this structure, since a contact surface contacting a part that needs to be treated inside the patient's body is small, the size and distribution of the RF electric field also becomes small. Thus, a problem may occur in that the treatment is carried out with limitations.

Additional methods that may be used for attaching the round-type electrodes (130, 140) may include laser spot welding, which is one of the most appropriate methods, as well as soldering, and other methods. Other methods may also include a method of performing coupling by using a screwing process, wherein the steering wires (110, 120) may be combined with the round-type electrodes (130, 140) by using an interference fit method for fitting the steering wires (110, 120) into holes formed on one side of the round-type electrodes (130, 140).

Herein, although the shape of the electrodes (130, 140) is limited to round-type electrodes (130, 140), the present invention shall not be limited only to this. Nevertheless, since the inserting part (100) is formed in a cylindrical shape, it will be preferable to form the electrodes (130, 140) to a round shape, accordingly. Additionally, it will also be preferable to form the end of the round-type electrodes (130, 140) to a dome shape. Referring to FIG. 4, each of the distal ends of the electrodes 130 and 140 has a half dome shape such that the electrodes 130 and 140 in combination form a dome. In addition, the electrode 130 has a semicircular recess 131 and the electrode 140 also has a semicircular recess 141 such that the first and second recesses 131 and 141 in combination form a circular hole 150. The circular hole 150 is provided at a most distal end portion of the dome formed by the first and second electrodes 130 and 140 in combination, as shown in FIG. 4. In case of forming each end to a dome shape, since the corresponding shape allows the electric field to be formed toward the front direction, it will be advantageous in that the treatment area can be expanded. In other words, in case of using the conventional steering wires, the electric field was weak at the front direction of the steering wires, and the electric field was stronger only on the side parts of the steering wires. Therefore, the above-described structure may enhance such downsides.

FIGS. 5A to 5C illustrate mimetic diagrams showing an example of controlling an RF electric field by forming an anisotropic gap between two round-type electrodes (130, 140) formed at an end of the electrodes (130, 140) of the epidural catheter according to an exemplary embodiment of the present invention.

In order to create an RF electric field, a gap shall exist between the electrodes (130, 140). Generally, the size of such gap is configured to be consistently equal. However, experiments have shown that, by varying the relative size of the gap, the distribution of the electric field can be adjusted. This has been directly applied to the catheter according to the present invention.

As an exemplary embodiment of the present invention, the two independent round-type electrodes (130, 140) are coupled to each steering wire (110, 120) so as to be symmetrical to one another.

As shown in FIG. 5B, in case the size of an upper gap is configured to be larger than the size of a lower gap, the RF electric field is formed in an area where the gap is smaller. In other words, the electric field is more likely to be optionally formed in an area where the gap is smaller rather than in an area where the gap is larger. This means that the intensity of the electric field may be adjusted by adjusting the size of the gap, and, accordingly, this means that the direction and distribution of the RF electric field being supplied inside the physical body may be adjusted. Such gap size may be determined at a time point where the round-type electrodes (130, 140) are combined with the steering wires (110, 120).

As described above, by adjusting the RF electric field, treatment may be carried out by irradiating a wanted amount (or size) of RF electromagnetic waves accurately on a wanted area. Thus, the treatment effect may be enhanced. And, by preventing RF electromagnetic waves from leaking from unwanted parts, a safer therapeutic (or surgical) procedure may be performed.

The location of the above-described gap will not be limited only to the upper part or lower part. And, therefore, for example, in case the cross-section is round, the gap may exist on two locations each being symmetrical to one another.

FIG. 6 illustrates a block diagram enabling an RF frequency to be varied and supplied to the epidural catheter according to an exemplary embodiment of the present invention. The conventional RF generator product formed an RF electric field at a fixed frequency of 500 kHz. However, according to a characteristic of the present invention, an RF electric field is formed at a variable frequency, which varies within a wide frequency range. When an RF generating frequency is changed (or varied), a resulting change in wavelengths may cause a penetration depth (or skin depth) of the RF electric field inside the physical body to vary accordingly. This allows the RF electric field to be accurately irradiated to a wanted depth, thereby enhancing the treatment effect. In other words, since the conventional product uses a fixed frequency, the penetration depth is uniform, which causes limitations in the treatment effect. The present invention has improved such downsides.

FIG. 7 illustrates a mimetic diagram showing an example of equipping the epidural catheter with a touch panel (105) and using a user interface (UI) to manipulate, through the touch panel (105), the catheter according to the exemplary embodiment of the present invention. The touch panel (105) includes an RF electric current application button allowing an RF electric current to be supplied to the steering wires (110 and 120). Although the manipulating part (104) may be configured of a general button, as shown in the drawing, various control settings may each be easily set to a wanted value by using a touch panel. Thus, convenience may be significantly enhanced for a doctor (or surgeon) performing the therapeutic (or surgical) procedure.

The exemplary embodiment of the present invention is presented herein for the description of the present invention. Therefore, it shall be noted that the exemplary embodiment of the present invention will not limit the scope of the present invention. Furthermore, it shall be understood by anyone skilled in the art that other various embodiments may also be applied within the technical scope and spirit of the present invention.

REFERENCE SIGNS AND NUMERALS

| | |
|---|---|
| 100: Inserting part | 102: Main body |
| 104: Manipulating part | 110, 120: Steering wire |
| 130, 140: RF electrode | |

What is claimed is:

1. An epidural catheter with an RF generation function, comprising:
   a main body;
   an inserting part being connected to the main body and configured to be inserted inside a physical body; and
   a manipulating part being provided in the main body and being connected to the inserting part or an internal assembly part of the inserting part, so as to manipulate the inserting part or to perform a function of the inserting part,
   wherein two steering wires are interpolated in the inserting part, the two steering wires being manipulated by the manipulating part so as to allow flexion of the inserting part to be controlled, wherein first and second electrodes are coupled to distal ends of the two steering wires, respectively, and the first and second electrodes are symmetrical and spaced apart from each other, wherein each of the first and second electrodes has a half dome shape such that the first and second electrodes in combination form a dome, wherein the first electrode has a first semicircular recess and the second electrode has a second semicircular recess such that the first and second recesses in combination form a circular hole, wherein the circular hole is provided at a most distal end portion of the dome formed by the first and second electrodes in combination.

2. The epidural catheter with an RF generation function of claim 1, wherein the inserting part is a form of a soft tube.

3. The epidural catheter with an RF generation function of claim 1, wherein the main body is equipped with an RF generator, wherein the two steering wires are connected to each of a cathode end and an anode end of the RF generator, and wherein the manipulating part comprises:
a lever being connected to proximal ends of the steering wires, so as to pull the steering wires or release pulling of the steering wires; and
an RF electric current application button allowing RF electric current to be supplied to the steering wires.

4. The epidural catheter with an RF generation function of claim 1, wherein a first RF magnetic field generated in a first area having a first distance between the first and second electrodes is greater than a second RF magnetic field generated in a second area having a second distance between the first and second electrodes, wherein the first distance is less than the second distance.

5. The epidural catheter with an RF generation function of claim 4,
wherein a direction and distribution of an RF electric field of the first and second electrodes is adjusted in accordance with the first and second distances between the first and second electrodes.

6. The epidural catheter with an RF generation function of claim 1, wherein a diameter of the first and second electrodes forming the dome shape is identical to a diameter of the inserting part.

7. The epidural catheter with an RF generation function of claim 1, wherein a first distance between upper portions of the first and second electrodes is different from a second distance between lower portions of the first and second electrodes.

* * * * *